US009072494B2

(12) United States Patent
Schnaars et al.

(10) Patent No.: US 9,072,494 B2
(45) Date of Patent: Jul. 7, 2015

(54) GENERATION OF VISUAL COMMAND DATA

(71) Applicants: Anja Schnaars, Nuremberg (DE);
Grzegorz Soza, Heroldsberg (DE);
Christian Tietjen, Fuerth (DE)

(72) Inventors: Anja Schnaars, Nuremberg (DE);
Grzegorz Soza, Heroldsberg (DE);
Christian Tietjen, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 160 days.

(21) Appl. No.: 13/837,394

(22) Filed: Mar. 15, 2013

(65) Prior Publication Data

US 2013/0245435 A1   Sep. 19, 2013

(30) Foreign Application Priority Data

Mar. 15, 2012   (DE) .................. 10 2012 204 063

(51) Int. Cl.
*G06K 9/00*   (2006.01)
*A61B 6/00*   (2006.01)
(Continued)

(52) U.S. Cl.
CPC .................. *A61B 6/5223* (2013.01); *A61B 6/03* (2013.01); *A61B 6/461* (2013.01); *A61B 6/504* (2013.01); *A61B 6/466* (2013.01); *G06T 19/00* (2013.01); *G06T 2210/41* (2013.01); *G06T 2219/021* (2013.01)

(58) Field of Classification Search
CPC ........ A61B 6/5223; A61B 6/03; A61B 6/461; A61B 6/504; A61B 6/466; G06T 19/00; G06T 2210/41; G06T 2219/021
USPC .................. 600/407–410, 437–469, 473–480; 382/128–132
See application file for complete search history.

(56) References Cited

U.S. PATENT DOCUMENTS

| 7,599,535 | B2 | 10/2009 | Kiraly et al. | |
| 7,711,165 | B2* | 5/2010 | Lesage et al. | 382/128 |
| 7,912,266 | B2* | 3/2011 | Fahmi et al. | 382/128 |

(Continued)

FOREIGN PATENT DOCUMENTS

| WO | WO-2009/019640 A2 | 2/2009 |
| WO | 2009/056147 A1 | 5/2009 |

OTHER PUBLICATIONS

Pu et al., "A Differential Geometric Approach to Automated Segmentation of Human Airway Tree," IEEE Transactions on Medical Imaging, vol. 30, No. 2, Feb. 2011, pp. 266-278.
(Continued)

*Primary Examiner* — Sanjay Cattungal
(74) *Attorney, Agent, or Firm* — Schiff Hardin LLP

(57) ABSTRACT

In a computerized method and system to generate visualization command data for two-dimensional visualization of a vascular tree of a vascular system from tomography data acquired via an imaging system, tomography data of the vascular tree are registered in the form of prepared tomography data that include acquired tomography data of the vascular tree in which said vascular tree is segmented at least in a region of surrounding structures, and in which are present a number of curve lines of vessels of the vascular tree that branch with one another. Inlets are shaped between curve lines that are adjacent and/or connected with one another via node points. Representation data are generated in which the inlets are arranged flat, adjoining one another in a two-dimensional presentation plane. The visualization command data are derived from the representation data and presented as an output.

15 Claims, 9 Drawing Sheets

(51) Int. Cl.
*A61B 6/03* (2006.01)
*G06T 19/00* (2011.01)

(56) References Cited

U.S. PATENT DOCUMENTS

| | | | |
|---|---|---|---|
| 8,163,003 B2* | 4/2012 | Boyden et al. | 623/1.13 |
| 8,358,819 B2* | 1/2013 | Wu et al. | 382/128 |
| 2005/0018885 A1 | 1/2005 | Chen et al. | |
| 2006/0023925 A1 | 2/2006 | Kiraly et al. | |
| 2007/0092864 A1* | 4/2007 | Reinhardt et al. | 435/4 |
| 2007/0238959 A1 | 10/2007 | John et al. | |
| 2009/0146008 A1 | 6/2009 | Thiele | |
| 2009/0322749 A1* | 12/2009 | Kassab et al. | 345/424 |
| 2010/0128954 A1* | 5/2010 | Ostrovsky-Berman et al. | 382/131 |
| 2010/0172554 A1* | 7/2010 | Kassab et al. | 382/128 |
| 2011/0093243 A1* | 4/2011 | Tawhai et al. | 703/2 |

OTHER PUBLICATIONS

Hijazi et al., "Fully-automatic branching reconstruction algorithm: application to vascular trees," Shape Modeling International 2010 (SMI2010), IEEE Computer Society, pp. 221-225.

Kanitsar et al., "Advanced Curved Planar Reformation: Flattening of Vascular Structures," Inst. of Computer Graphics and Algorithms, Vienna University of Technology.

Kiraly et al., "2D display of a 3D tree for pulmonary embolism detection," International Congress Series 1281, 2005, pp. 1132-1136.

Saroul et al., "Distance Preserving Flattening of Surface Sections," IEEE Transactions on Visualization and Computer Graphics, vol. 12, No. 1, Jan.-Feb. 2006, pp. 26-35.

Floater, "Parametrization and smooth approximation of surface triangulations," Computer Aided Geometric Design, vol. 14, 1997, pp. 231-250.

* cited by examiner

3', 15

3", 15

1', 15

1", 15

GENERATION OF VISUAL COMMAND DATA

BACKGROUND OF THE INVENTION

1. Field of the Invention

The present invention concerns a method to generate visual command data for two-dimensional visualization of a vascular tree of a vascular system from tomography data acquired with an imaging system, as well as a command data derivation system for the same purpose.

2. Description of the Prior Art

The two-dimensional visualization of image data (i.e., tomography data) from vascular systems (especially vascular trees) from an imaging tomography exposure serves to enable a viewer to be shown an overview of the often very complex structures of the respective vascular system. Even when the vascular systems (for example blood vessel systems, but also other vascular systems formed as branching hollow organs, such as the lymphatic system, the bronchial tree or others) exist in a widely branching and correspondingly complex three-dimensional tree structure, the viewer must be able to quickly be given an overview on a screen or using a computer printout. In practice, this overview is inevitably presented in two dimensions. The evaluation of the topology of a vascular tree then forms an important basis of evaluation for the analysis of functional pathologies in medicine. A suitable visualization of the vascular tree hereby represents an essential basis for a qualitative assessment.

However, conventional presentation methods for both two-dimensional and three-dimensional presentation return only a defined section of the total information content of the tomography data. Either losses in clarity arise, or only partial sections of a vascular tree can be presented to the observer at one time. The unfolding of a vascular tree enables the representation of its topology without superposition of structures in a single presentation and is usable in a versatile manner.

Essentially, two methods exist that attempt to present an unfolded vascular tree. In multi-path CPR that is described in Kanitsar A. et al.: "Advanced Curved Planar Reformation Flattening of Vascular Structures" in: IEEE Visualization, IEEE Computer Society Press; 2003. P. 43-50, slices that are projected in one plane are created along a single vascular center line (i.e. a curve line or, respectively, more precisely a center line). The arrangement of adjacent vascular representations subsequently takes place with the aid of recursively circumscribing sub-trees. In the approach from Kiraly et al. ("2D Display of a 3D Tree for Pulmonary Embolism Detection" in: CARS Vol. 1281; 2005. P. 1132-1136), what is known as an intensity projection that is subsequently arranged in a tree diagram is generated along each vascular center line on the basis of the vascular surface. Both methods generate a very schematic representation of the vascular tree. Furthermore, the multi-path CPR is especially more suitable for less complex vascular trees. Exemplary embodiments for this would be pathological cardiac vessels or peripheral vessels. An additional, relevant method generates a slice through a vessel with the aid of Coons surfaces. This approach is described in Saroul L et al.: "Distance Preserving Flattening of Surface Sections" IEEE TVCG, 2006; 12; P. 26-35. These Coons surfaces here are subsequently flattened at a point or, respectively, in a curve of interest. However, this method is only conceived for a single vessel, and not for a vascular tree.

SUMMARY OF THE INVENTION

Against this background, it is an object of the present invention to provide an improved two-dimensional visualization of vascular trees that is particularly suitable to image even more complex (i.e. additionally branched) vascular systems for a user.

This object is achieved by a method according to the invention that includes at least the following steps implemented in a computerized processor:

register (receive) tomography data of the vascular system that are acquired with the aid of the imaging system in the form of prepared tomography data that include the acquired tomography data of the vascular tree, in which prepared tomography data the vascular tree is segmented at least into regions of circumadjacent structures, and in that are present a number of curve lines of vessels of the vascular tree that branch with one another, shaping of inlets between adjacent curve lines and/or curve lines connected with one another via node points, adaptation of the representation data such that the inlets are arranged adjoining one another in a planar manner in a two-dimensional presentation plane, derivation of visualization command data from the representation data, and output of the visualization command data.

In general, a "vascular system" as used herein means an animal or person (in particular a blood vessel system). The vascular tree entirely or partially maps to this vascular system.

As a first step of the method, a provision of prepared tomography data takes place. This provision can include the corresponding preparation of the tomography data; however, they can also include a simple receipt of these data from a unit that has prepared these tomography data or stores the previously prepared tomography data. Such a unit can thus be a preparation unit and/or a memory unit.

The prepared tomography data include or represent curve lines of the vascular tree to be inspected, i.e., curve lines within the vascular tree. In the inventive method, such curve lines preferably include middle lines (also called center lines) of the appertaining vessels, i.e. curve lines that proceed along central points of the vessel in its cross sections that are transverse to its principal curve. The center lines therefore represent the principle center curve of a vessel and are connected with one another at node points of the vascular tree, i.e. are joined to one another so that a curve line (or center line) tree results that represents the vascular tree itself. Determination methods for such center lines and methods to connect the center lines at node points are known to those skilled in the art. Since the center lines only respectively represent (i.e. representatively, schematically reproduce) the principle curve of the vessels and its center, the selection of any specific method for determination thereof within the scope of the method according to the invention is not mandatory, but an optimally precise reproduction of the curve (and in particular the respective center of the vessel) is naturally advantageous because this increases the representational accuracy (and therefore the diagnostic significance) of the curve line tree.

The output data that are used (thus the prepared tomography data) thus include both the original volume data set and a segmented vascular tree that can be acquired manually or automatically, and may be acquired in advance. This vascular tree preferably exists as a graph structure in which information regarding both the vascular curve and their approximated vessel contours of the individual vascular tree branches are present.

The curve is described by means of the curve line, preferably by means of vascular center lines which basically represent an ordered point series scanned at uniform intervals.

Information regarding the local vessel contour is associated with each center line point via a circle radius variable.

Components known as inlets (i.e. surfaces) are then shaped (molded) or fitted between the individual adjacent curve lines in the prepared tomography data. The inlets can be designed as flat (i.e. planar) planes, but they are preferably curved planes due to the irregularities of the curve lines as well as their principle curves. In particular, those curve lines between which no additional curve line is present (i.e. is arranged or was determined in the preparation of the tomography data) along an inlet that can be spanned by said curve lines, are designated as adjacent curve lines.

It is then determined how a two-dimensional representation of the tomography data can take place on the basis of the inlets that are determined in such a manner, in which the inlets are projected in an arrangement adjoining one another on a planar surface. This step can be designated as the unfolding of the vascular tree. The method according to the invention thus generates a curved slice surface that is oriented on the vascular topology, and this slice surface is ultimately unfolded.

The representation data that represent this manner of unfolding and from which the visualization command data are then derived, which enable an output unit to display the corresponding representation, result from the determined manner of how the vascular tree should be unfolded. The relaying of the visualization command data therefore takes place directly or indirectly (for example via a memory unit) to such an output unit.

A planar (thus two-dimensional) imaging of the entire vascular tree is thus possible with the method according to the invention, in the case of a vascular tree of a vascular system with a large number of branches. It is thus possible for the first time to image even very complex vascular structures so that a viewer can in practice conduct a finding along all determined vascular trees at a glance. In contrast to conventional approaches, this takes place in accordance with the invention by that the vascular tree being two-dimensionally presented as a whole (i.e. not in segments) when it exists branched widely (multiply) in a complex three-dimensional structure. The representation data thus also include derived image data that are derived from the original image data (i.e. the image acquisition data from a tomography exposure). The derived data thereby go beyond the mere representation of the curve lines and in particular include color-coded or greyscale-coded image data of the vascular tree itself, preferably such image data from which even surface structures inside the vessel can themselves be registered in addition to the curves of the vascular tree.

A derivation system according to the invention is operated to implement the method according to the invention. A system of the aforementioned type accordingly comprises at least the following components according to the invention:

- a provision unit provides (is a source of) prepared tomography data that include acquisition data of the vascular tree in which the vascular tree is segmented, at least in a region of surrounding structures, and in which is present a number of curve lines of vessels of vascular tree that are branched with one another,
- a shaping unit that is designed to shape inlets between adjacent curve lines and/or curve lines that are connected with one another via node points,
- an adaptation unit that, during operation, adapts the representation data such that the inlets are arranged adjoining one another in a planar manner in a two-dimensional representation plane,
- a derivation unit that derives the visualization command data from the representation data, and
- an output unit that makes the visualization command data available as a humanly perceptible presentation.

For example, the provision unit can be realized as a processing unit that prepares the tomography data, but can also be designed as an input interface that only receives and relays the prepared tomography data directly or indirectly from such a processing unit.

Interfaces—thus for example the provision unit or the output unit—do not necessarily need to be designed as hardware components, but can be realized as software modules, for example when the (prepared) tomography data can be accepted from a different component that has already been realized at the same apparatus, or must be passed to a different component only in software. The interfaces can likewise include hardware and software components, for example a standard hardware interface that is specially configured by software for a particular usage purpose. Moreover, multiple interfaces can also be assembled into a common interface, for example an input/output interface.

Overall, a majority of the components for realization of the derivation system in the manner according to the invention—in particular the provision unit, the shaping unit, the adaptation unit and the derivation unit—can be realized wholly or in part in the form of software modules in a processor.

The invention therefore also encompasses a non-transitory, computer-readable data storage medium that can be loaded directly into a processor of a programmable derivation system, that includes stored program codes in order to execute all steps of a method according to the invention when the program product is executed at the derivation system.

The invention also encompasses a tomography system with an acquisition unit and a derivation system according to the invention. It is particularly advantageous when the derivation system is part of a tomography system, because then the visualization can be made at the image data acquisition site or in the same computer system.

The vascular tree preferably constitutes vessels of the liver. Because of their structure for supplying and discharging blood vessels with a high degree of branching, which varies from person to person, these vessels exhibit a particularly high degree of complexity in which multiple trees also intersect within the liver. Particularly in the liver, knowledge about its vascular tree topologies allows a more detailed analysis, planning and implementation of surgical procedures.

In order to continue to ensure blood supply to remaining tissue after a partial resection of the liver, the course of important vessels should likewise be known. A representation that reproduces both the extent of the vessels in the region of the resection and that clearly reproduces the connection and branching structure is consequently essential. In contrast to this, the tracking of a path along the liver vascular system is of significant interest in particular in the field of tumor treatment. When administering a bolus of a treatment agent to a partial vascular tree, the bolus must be administered accurately via a catheter (probe) in order to reach only the target region. In order to enable an optimally simple navigation of the probe, the corresponding path in the representation should not be occluded by other structures. It is in such a context that the method according to the invention can offer a particularly comprehensive overview.

The prepared tomography data can be registered in three alternative ways:

1. The tomography data can be provided as tomography data that are completely prepared in advance. This means that they were prepared in a unit that is upstream of the system according to the invention, such that they need only be imported via a corresponding input interface.

2. The registration of the tomography data can include a provision of raw tomography data in which the vascular tree is then segmented, at least per region of surrounding structures, within the scope of the method workflow according to the invention. As a result, the curve lines of the vascular tree are then also derived.

3. The registration of the tomography data can include a provision of segmented tomography data in which the vascular tree is segmented at least per region of surrounding structures. Within the scope of the method workflow according to the invention, a number of curve lines of vessels of the vascular tree are then derived in the segmented tomography data.

In these three alternatives, tomography data at different levels of preparation quality are thus provided and registered. The first alternative has the advantage that complicated segmentation and derivation steps have not yet been incurred during the implementation of the method according to the invention. Moreover, this means that tomography data that were also already surveyed earlier can be processed and visualized accordingly with the aid of the method according to the invention.

In contrast to this, the other two alternatives have the advantage that the derivation (and in the second variant) possibly also the segmentation take place such that the prepared tomography data are matched optimally to the requirements within the scope of the method according to the invention.

The inlets are preferably generated by means of pre-order traversal along the curve lines. The pre-order method (which is based on the fitting of a binary tree to the curve line) is a method in which a root tree is formed in which each node has at most two child nodes. With regard to this curve lines with their branches, this means that a direction deviation along the curve line is always formed when one curve line forms a node point with another curve line. The pre-order traversals are thus boundary lines of the inlets that are bounded by the curve lines, such that an inlet can be created between curve lines associated with one another in an internal region formed by a pre-order traverse.

In order to define the geometric figure of the inlets, it has proven to be particularly reliable and simple to subdivide these inlets into a number of individual surfaces, wherein each of these individual surfaces then preferably, respectively derives from a predefined point of a curve line (i.e. is assigned to this). Such a predefined point is preferably a node point of a curve line at which it strikes another curve line, or an end point of the curve line (i.e. the point of the curve line at which it ends). This ending of the curve line can be due to the corresponding vessel either ending there or branching again at this point, but the further branches are no longer represented by further curve lines. It is thus then an end point of the curve line determination. This curve line determination can therefore end both because the further determination of the curve line was no longer pursued in the preparation of the tomography data (for example due to the computing capacity, too low an image resolution etc.) or because it has been defined by the user that only a specific region of the tomography data should be examined in detail, and the further branches of the vascular tree as of the end point fall outside of this region.

Subdividing the inlets into a number of (preferably multiple) individual surfaces assists in reducing the unevennesses in the inlets that, in practice, inevitably result due to the different alignments of the curve lines, and additionally provides the possibility of a fine subdivision precisely given larger-area inlets. The individual surfaces are also preferably not planar, but rather are formed uneven and particularly preferably (just like the inlets) as (possibly composite) Coons surfaces in which the curve line can be integrated in the form of a Bézier curve. At the outside lines, they therefore respectively reproduce the curve of the curve lines that cause them, and their inner curve is correspondingly shaped to the curve of this curve line that they significantly bound.

In the formation of the individual surfaces, it has proven to be particularly advantageous (because of significant and optimally fine-precision determination) when the individual surfaces are preferably bounded by the following boundary lines:
  a first curve line of the vascular tree along their extent from a first node point up to an end point. This end point can be either a second node point or a curve end point of the determined curve of the curve line.
  a connecting line from the first node point to a focal point of the respective inlet that is formed by focal point calculation from all points of the curve line defining the inlet that surround said inlet.
  a connecting line from the end point to the focal point of the respective inlet.

Individual surfaces arranged in a star shape therefore result emanating from the focal point, which individual surfaces in combination form the inlet. In the end result, the focal point thereby defines the point of the greatest deviation from a planar surface.

The more acute the angle of inclination of the individual surfaces meeting one another along a curve line, the stronger the distortion precisely in the region of the vessels given the later, planar representation of the vascular tree. Therefore, the shape of the inlets and/or of the individual surfaces is preferably adapted depending on a locally present vessel contour of the vessel represented by a local curve line.

This preferably takes place on the basis of the already generated slice surfaces (inlets or individual surfaces) by the generation of what is known as a vascular band that intersects the vessel with a straight line in cross section. Such a method preferably takes place as follows: the inlets and/or the individual surfaces are oriented on vessel contour lines to form what is known as a vascular band skeleton that is determined as follows:
  a) insert flat, individual surfaces between adjacent curve lines and/or curve lines connected with one another via node points,
  b) locally determine vessel contour lines at a first slice surface of a vessel along a selected curve line,
  c) form a vertical line along the first slice surface, which vertical line is formed by the mean angle between
    a flat, first individual surface along the selected curve line in the first slice surface,
    a flat, second individual surface that adjoins the first slice surface along the selected curve line,
  d) form a straight auxiliary line orthogonal to the vertical line, and determine intersection points of the auxiliary line with the vessel contour line on both sides of the vessel contour,
  e) implement Steps b) through d) along the course of the entire curve line using additional slice surfaces along this curve, and form two orientation lines from the shortest connections of the intersection points along both sides of the vessel contour,
  f) orient the curve of the individual surfaces and/or inlets along the respective orientation lines nearest the flat individual surfaces and/or inlets.

At each point of the curve line, a plane is thus generated that is situated orthogonal to the local direction of the curve line (local tangent vector). By intersecting this plane with the already generated individual surface, the current exit points can be determined from the contour region in cross section along the respective curve line. These exit points are subsequently each rotated with the same angles in the corresponding planes around the respective point of the curve line in the slice surface so that they enclose a 180° angle with the point of the curve line. The exit points shifted in such a manner—i.e. the intersection points of the auxiliary line with the vessel contour line—form two orientation lines strung together along all slice surfaces.

The straight auxiliary line (that is arranged at the same angle relative to both individual surfaces due to the vertical alignment of the vertical line of both of the aforementioned individual surfaces) consequently serves as a presentation line of the vessel: the auxiliary lines that are connected with one another along the individual slice surfaces of the vessel form a representation surface of the vessel in the planar representation. Distortion effects are thereby reduced to an absolute minimum specifically in the region of interest of the vessels themselves in the ultimate planar representation of the vascular tree.

So that a continuous transition of the orientation lines in branching regions (or node points) is created, the newly calculated points in the end region of the respective meeting curve lines are preferably interpolated by means of a low-pass filter. The orientation lines are thus aligned to one another via interpolation by means of a low-pass filter in a branching region of two curve lines. The slice surface that is necessary for the unfolding can be generated based on the vascular band skeleton that is generated in such a manner.

The curve lines of the vascular tree must subsequently be connected. However, instead of the original curve lines, the generated vascular band skeleton with the two orientation lines of the vessel is now used. For this purpose, a surface is formed between two orientation lines associated with a curve line, which surface is advantageously formed as a Coons surface consisting of four edge curves. The vascular band skeleton thereby preferably corresponds to the respective opposite edge curves. In the branching region, the surfaces are generated similar to those in the inlets. The vertices of the vascular band skeleton thereby serve to generate the edge curves.

In a further step, the individual surfaces and/or inlets that are oriented in Step f) are subsequently smoothed using geometric filtering methods (in particular a Laplace filtering method). Inlets with simpler shapes, with fewer individual surfaces, thereby result, such that the unfolding of the vascular tree can be implemented in a less complicated manner.

The vascular tree is now unfolded on the basis of the curved or, respectively, deformable slice surface that is now formed, which represents the curve of the vascular tree together with all of its branches. This adaptation of the representation data includes the following preferred steps:

determine a number of bordering edges of the vascular tree,
determine distances of the bordering edges from one another,
arrange the bordering edges at the same distance relative to one another along a convex outer line,
flat arrangement of the inlets within the convex outer line, bounded by said outer line.

The boundary edges of the vascular tree are the points that border said vascular tree.

The planar embedding of the entire slice surface (i.e. the entirety of all inlets or, respectively, individual surfaces) thus takes place with the aid of an optimization method from the field of mesh parameterization. For efficiency reasons, a method is preferably selected that transfers the edge of the entire slice surface into a region that is already convex (for example in a circle region). The size ratio of the distance of a single edge from all edges in the image is thereby ensured.

The flat arrangement that then follows particularly preferably takes place based on mean values, advantageously on the basis of the mean method proposed in Floater M S: "Parameterization and Smooth Approximation of Surface Triangulations," Computer Aided Geometric Design, 1997; 14(3), P. 231-250, which has angle-preserving properties so that the angles of the vascular tree can be maintained as important parameter values in the two-dimensional reproduction. The linear equation system that results from this is preferably solved by means of the Gaussian elimination method and an LU decomposition.

The method according to the invention concerns the two-dimensional representation of a vascular tree, wherein this vascular tree can also be present only in part. It is hereby also to be mentioned that a user is preferably enabled to select a specific part of a vascular tree for presentation by means of control commands. A selection presentation of the selected part of the vascular tree is then preferably initiated on the basis of such control commands, meaning that the visualization command data are designed so that only the selected portion of the vascular tree (possibly with the tissue surrounding it) is shown.

DESCRIPTION OF THE PREFERRED EMBODIMENTS

Figure 1:
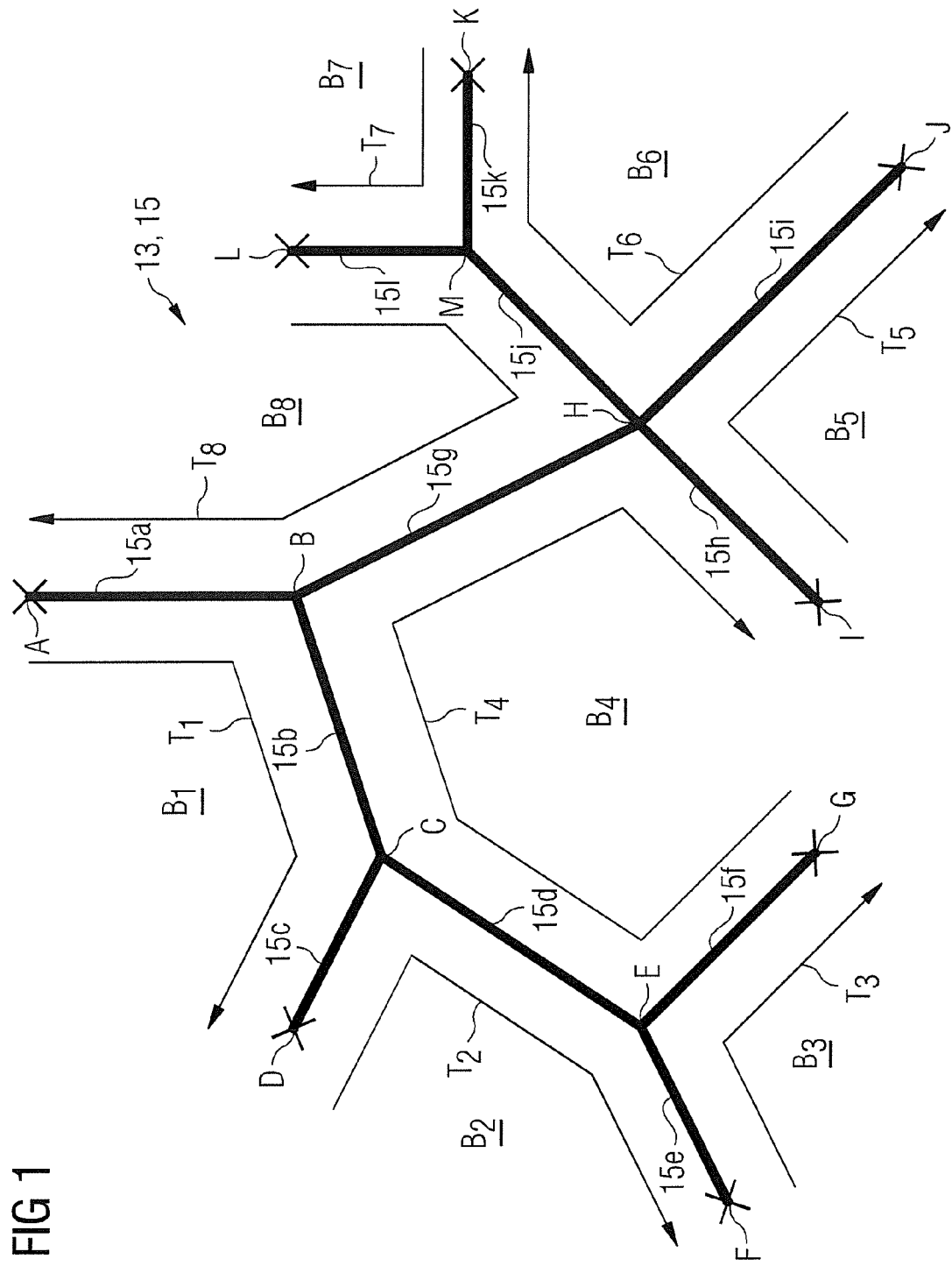
FIG. 1 is a schematic representation of a vascular tree of a vascular system within prepared tomography data for implementation of an exemplary embodiment of the method according to the invention.

FIG. 1 schematically shows a vascular tree 13 of a vascular system 15 that here is represented by curve lines 15a, 15b, 15c, 15d, 15e, 15f, 15g, 15h, 15i, 15j, 15k, 15l, namely by middle lines—also called center lines—15a, 15b, 15c, 15d, 15e, 15f, 15g, 15h, 15i, 15j, 15k, 15l. These curve lines 15a, 15b, 15c, 15d, 15e, 15f, 15g, 15h, 15i, 15j, 15k, 15l were derived from tomography data of the vascular system 15 and exist in a graph structure in which information is present regarding both the vessel course and the approximated vessel contours of the individual vascular tree branches of the vascular tree 13. This information, the curve lines 15a, 15b, 15c, 15d, 15e, 15f, 15g, 15h, 15i, 15j, 15k, 15l and the tomography data themselves together form what are known as prepared tomography data.

The curve lines 15a, 15b, 15c, 15d, 15e, 15f, 15g, 15h, 15i, 15j, 15k, 15l are connected with one another at node points B, C, E, H, M. These node points node points B, C, E, H, M are also regarded as end points of the individual curve lines 15a, 15b, 15c, 15d, 15e, 15f, 15g, 15h, 15i, 15j, 15k, 15l, just like end points A, D, F, G, I, J, K, L, which are not node points but also mark the end of a respective one of the curve lines 15a, 15b, 15c, 15d, 15e, 15f, 15g, 15h, 15i, 15j, 15k, 15l.

To implement the method, in the following what are known as inlets $B_1$, $B_2$, $B_3$, $B_4$, $B_5$, $B_6$, $B_7$, $B_3$ are formed within pre-order traverses $T_1$, $T_2$, $T_3$, $T_4$, $T_5$, $T_6$, $T_7$, $T_8$ that reproduce the curve of the curve lines 15a, 15b, 15c, 15d, 15e, 15f, 15g, 15h, 15i, 15j, 15k, 15l. The inlets $B_1$, $B_2$, $B_3$, $B_4$, $B_5$, $B_6$, $B_7$, $B_3$ are defined in that they respectively lie between curve lines 15a, 15b, 15c, 15d, 15e, 15f, 15g, 15h, 15i, 15j, 15k, 15l that either are connected with one another via node points B, C, E, H, M, or between which are arranged no other curve lines 15a, 15b, 15c, 15d, 15e, 15f, 15g, 15h, 15i, 15j, 15k, 15l of one and the same vascular tree 13 (or a defined vascular tree segment). The surface of an inlet $B_1$, $B_2$, $B_3$, $B_4$, $B_5$, $B_6$, $B_7$, $B_3$ is thus formed from at least two curve lines 15a, 15b, 15c, 15d, 15e, 15f, 15g, 15h, 15i, 15j, 15k, 15l in a chain, which curve lines are connected with one another via node points B, C, E, H, M, wherein the ends of the chain—i.e. end points A, D, F, G, I, J, K, L that are not node points—are connected with one another. Given a vascular tree with only one fork (not shown), the chain consists of precisely two curve lines that are connected with one another.

Figure 2:
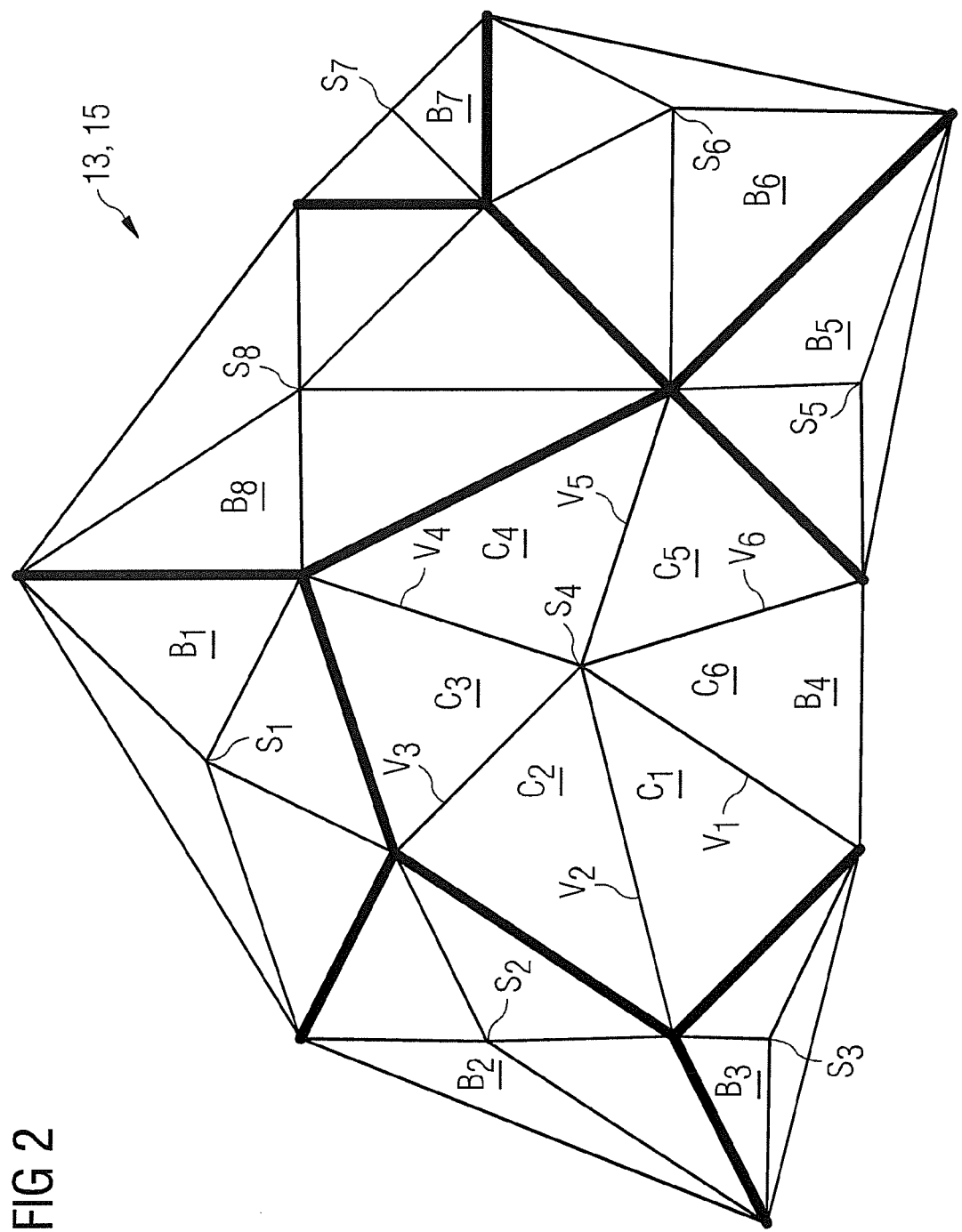
FIG. 2 is a schematic representation of the same vascular tree during a first processing step of an exemplary embodiment of the method according to the invention.

In the present case, the inlets $B_1$, $B_2$, $B_3$, $B_4$, $B_5$, $B_6$, $B_7$, $B_8$ formed in a method that is explained in detail using FIG. 2:

A focal point S1, S2, S3, S4, S5, S6, S7, S8 is respectively formed from all points of the respective curve lines adjoining an inlet B1, B2, B3, B4, B5, B6, B7, B8, which focal point S1, S2, S3, S4, S5, S6, S7, S8 defines a central point of the respective inlet B1, B2, B3, B4, B5, B6, B7, B8 from which connection lines are aligned in the direction of all end points A, B, C, D, E, F, G, H, I, J, K, L, M, which connecting lines here are designated only with reference to a selected inlet B4: six connecting lines V1, V2, V3, V4, V5, V6 run from the focal point S4 of the inlet B4 to the end points G, E, C, B, H, I of the curve lines 15f, 15d, 15b, 15g, 15h (see FIG. 1). These connecting lines V1, V2, V3, V4, V5, V6, together with the respective curve lines 15f, 15d, 15b, 15g, 15h that they enclose, define six individual surfaces C1, C2, C3, C4, C5, C6 that are realized as Coons surfaces C1, C2, C3, C4, C5, C6. Together, these Coons surfaces C1, C2, C3, C4, C5, C6 form the selected inlet B4. The assembled Coons surfaces of all inlets B1, B2, B3, B4, B5, B6, B7, B8 together form a three-dimensional slice surface that represents the vascular tree 13.

Figure 3:
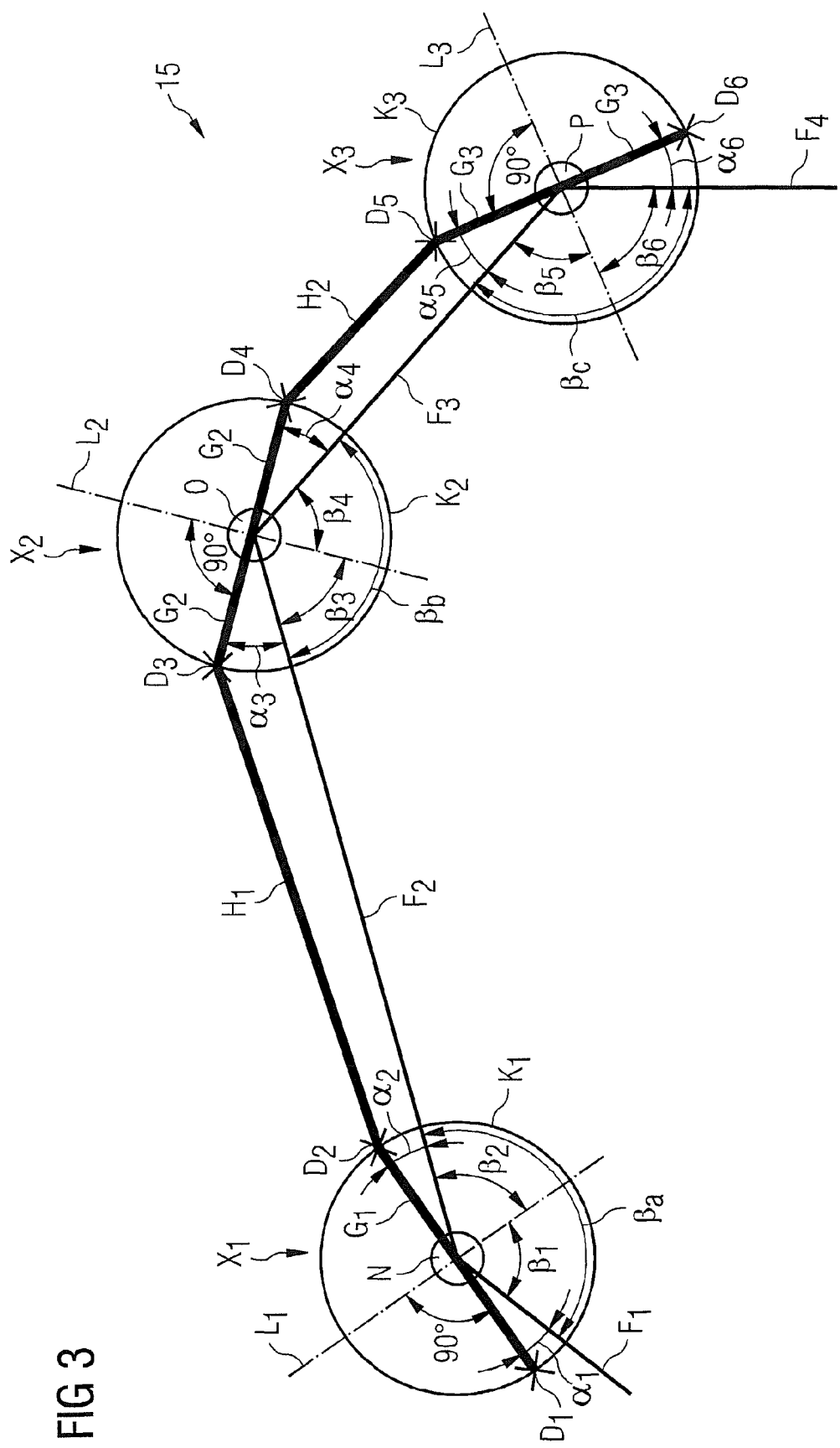
FIG. 3 is a schematic representation of vessels of the same vascular tree during a second processing step of an exemplary embodiment of the method according to the invention.

If this three-dimensional slice surface were now unfolded into two dimensions so that it is arranged in a common, flat plane, significant distortions would result via calculation in the region of the vessels of the vascular tree 13 that are to be depicted. These distortions turn out to be greater the more acute the angle of inclination of adjoining inlets $B_1$, $B_2$, $B_3$, $B_4$, $B_5$, $B_6$, $B_7$, $B_8$ or, respectively, individual surfaces $C_1$, $C_2$, $C_3$, $C_4$, $C_5$, $C_6$ along the respective curve lines 15a, 15b, 15c, 15d, 15e, 15f, 15g, 15h, 15i, 15j, 15k, 15l. Therefore, the representation is refined again before the unfolding of the vascular tree 13, which is schematically depicted in FIG. 3:

For this, what is known as a vascular band skeleton is formed: three vessels $X_1$, $X_2$, $X_3$ are schematically shown here in section along their longitudinal axis. Flat individual surfaces $F_1$, $F_2$, $F_3$, $F_4$—which can, for example, be the inlets or, respectively, individual surfaces formed as stated above—run between the vessels $X_1$, $X_2$, $X_3$ or, respectively, up to additional vessels that are now shown. Within the first vessel $X_1$, at a point N (of the curve line of the first vessel $X_1$) a first individual surface $F_1$ thereby runs up against a second individual surface $F_2$ at an angle $\beta_a$, which second individual surface $F_2$ ends at a point O of the curve line of the second surface $X_2$. There the second individual surface $D_2$ hits a third individual surface $F_3$ at an angle $\beta_b$, which third individual surface $F_3$ connects the point O of the curve line of the second vessel with a point P of the curve line of the third vessel $X_3$. The third individual surface $F_3$ here hits a fourth individual surface $F_4$ at an angle $\beta_c$, which fourth individual surface $F_4$ continues to a further vessel (not shown).

The more acute the angles $\beta_a$, $\beta_b$, $\beta_c$, the greater the distortion of the image representation will be given planar arrangement of the vascular tree along the individual surfaces $F_1$, $F_2$, $F_3$, $F_4$ specifically in the region of the vessels $X_1$, $X_2$, $X_3$. Therefore, it is specifically these regions that are handled specially. This takes place in that a respective vertical line $L_1$, $L_2$, $L_3$ is formed in each vessel $X_1$, $X_2$, $X_3$ at the (first) slice surface shown here, the vertical lines $L_1$, $L_2$, $L_3$ respectively halving the angles $\beta_a$, $\beta_b$, $\beta_c$: the angle $\beta_a$ is thereby divided into a first angle $\beta_1$ between the first partial surface $F_1$ and the vertical line $L_1$ and a second angle $\beta_2$ between the vertical line $L_1$ and the second partial surface $F_2$. The angle $\beta_b$ is divided into a third angle $\beta_3$ between the second partial surface $F_2$ and the vertical line $L_2$ and a fourth angle $\beta_4$ between the vertical line $L_2$ and the third partial surface $F_3$. Finally, the angle $\beta_c$ is divided into a fifth angle $\beta_5$ between the third partial surface $F_3$ and the vertical line $L_3$ and a sixth angle $\beta_6$ between the vertical line $L_3$ and the fourth partial surface $F_4$. Respective straight auxiliary lines $G_1$, $G_2$, $G_3$ are then arranged in the same slice surface, orthogonal to these vertical lines $L_1$, $L_2$, $L_3$. The first auxiliary line $G_1$ thereby forms a first angle $\alpha_1$ relative to the first partial surface $F_1$ and a second angle $\alpha_2$ relative to the second partial surface $F_2$, wherein $\alpha_1$ and $\alpha_2$ are equal in terms of their absolute value. The second auxiliary line $G_2$ forms a third angle $\alpha_3$ relative to the second partial surface $F_2$ and a fourth angle $\alpha_4$ relative to the third partial surface $F_2$, wherein $\alpha_3$ and $\alpha_4$ are equal in terms of their absolute value. The third auxiliary line $G_3$ forms a fifth angle $\alpha_6$ relative to the third partial surface $F_3$ and a sixth angle $\alpha_6$ relative to the fourth partial surface $F_4$, wherein $\alpha_5$ and $\alpha_6$ are equal in terms of their absolute value. The auxiliary lines $G_1$, $G_2$, $G_3$ proceed through the respective points N, O, P of the curve lines of the respective vessels $X_1$, $X_2$, $X_3$, meaning that they form a 180° angle at this point.

Intersection points $D_1$, $D_2$, $D_3$, $D_4$, $D_5$, $D_6$ that precisely oppose one another along the vessel contour in the shown first slice surface result where the auxiliary lines $G_1$, $G_2$, $G_3$ respectively intersect with the vessel contour lines $K_1$, $K_2$, $K_3$ of the three vessels $X_1$, $X_2$, $X_3$. These intersection points $D_1$, $D_2$, $D_3$, $D_4$, $D_5$, $D_6$ are to be used to form the vascular band skeleton: additional such intersection points are determined by implementing the same method steps along a next slice surface, i.e. into the image in the representation of a parallel surface that is present here. All determined intersection points of a vessel along the curve of its entire curve line are connected with one another and form two orientation lines from the shortest connections of the intersection points along both sides of the vessel contour.

These orientation lines now serve to reorient the inlets or, respectively, individual surfaces that were previously described using FIGS. 1 and 2, namely to preferably precisely border along these orientation lines. The surfaces of the inlets, or the individual surfaces, are thus now oriented on the orientation lines instead of on the respective curve lines. An essentially flat plane that is formed from the composed auxiliary lines $G_1$, $G_2$, $G_3$ along the respective vessel curves results in the regions of the vessels $X_1$, $X_2$, $X_3$ themselves. This plane then serves approximately as a presentation plane of the vessel in the later planar representation after unfolding the vascular tree 13. The surfaces are actually generated along the curve lines of the vessels with Coons surfaces consisting of four edge curves. The orientation lines thereby correspond to two respective, opposite edge curves of the Coons surfaces. In the branching region of two vessels (i.e. at node points), the surfaces are generated analogous to the inlets (meaning again with subdivision of the inlets into partial surfaces). The vertices of the orientation lines (i.e. of the vascular band skeleton) thereby serve for the generation of the edge curves of the inlets.

Figure 4:
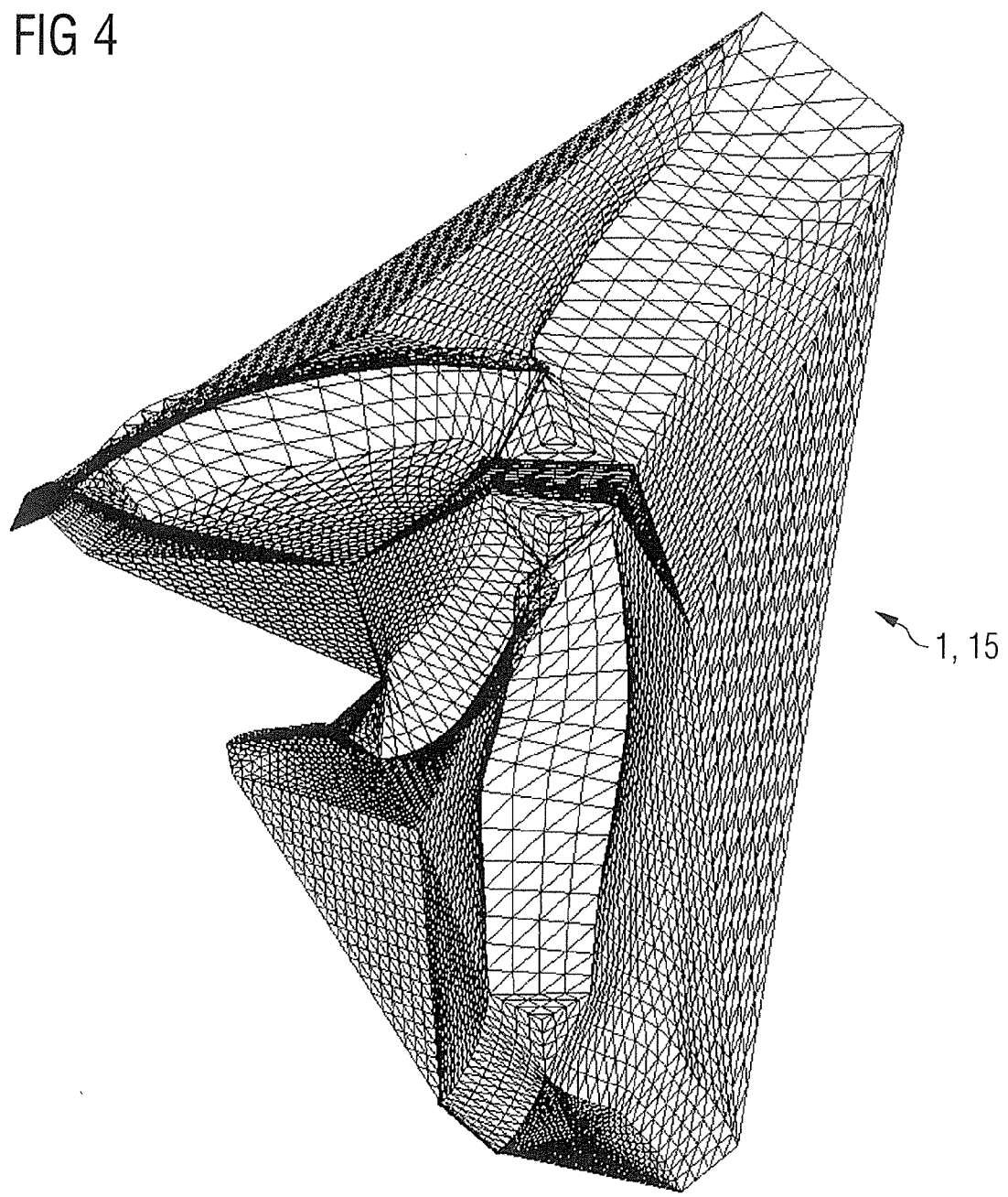
FIG. 4 is a three-dimensional representation of the same vascular system after the implementation of the first two processing steps.
Figure 5:
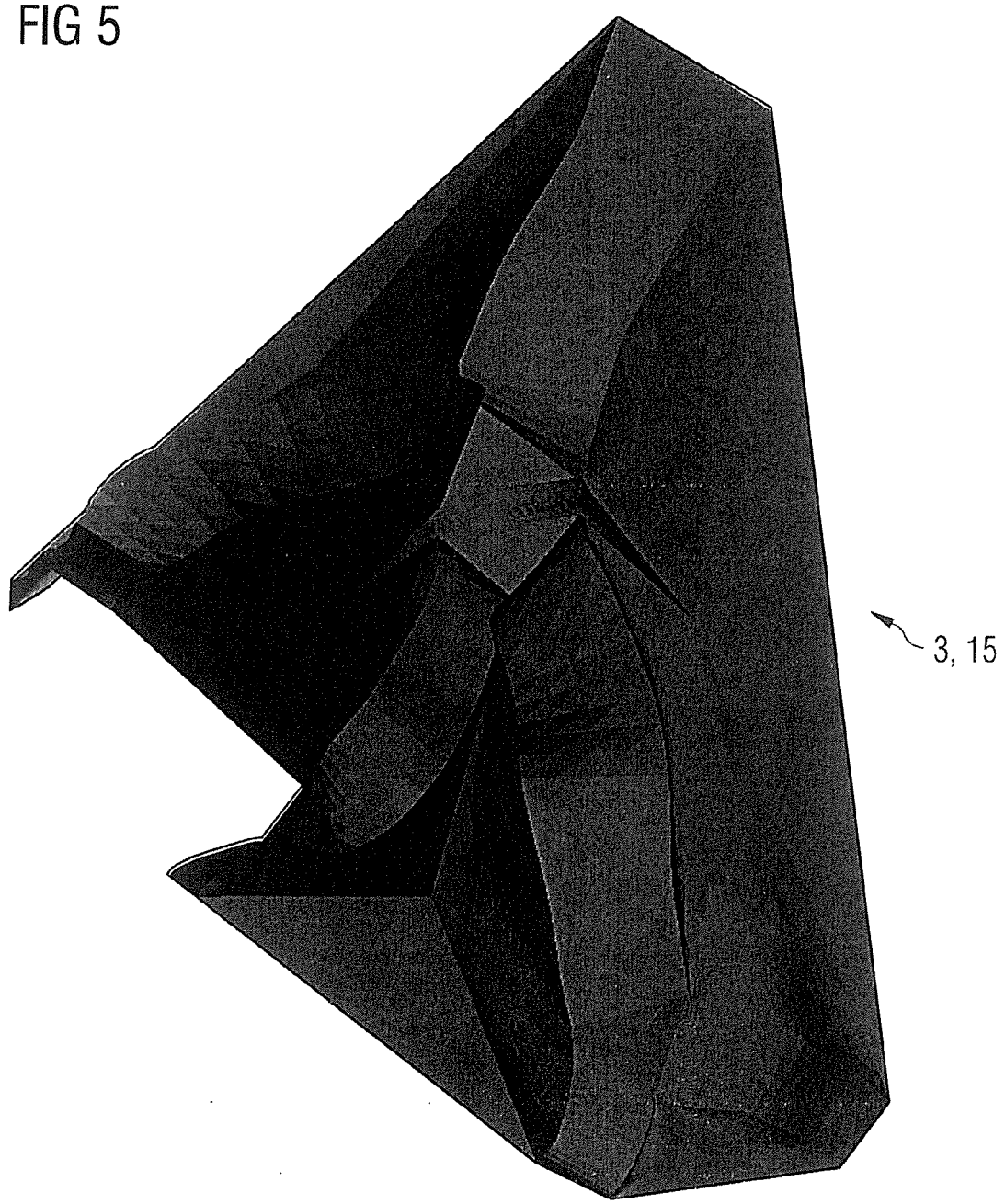
FIG. 5 is a three-dimensional representation of the same vascular system after a third processing step of an exemplary embodiment of the method according to the invention.

FIG. 4 shows a mesh presentation 1 of the vascular system 15 on the basis of the individual Coons surfaces generated in such a manner. In a greyscale-coded resolution presentation, a surface model 3 of the tree structure of the vascular tree 13 as it is shown in FIG. 5 results from this. This surface model was additionally smoothed with a Laplace filter so that the number of individual surfaces (i.e. the triangles within the inlets) is reduced, which facilitates the following unfolding of the surface model 3.

Figure 6:
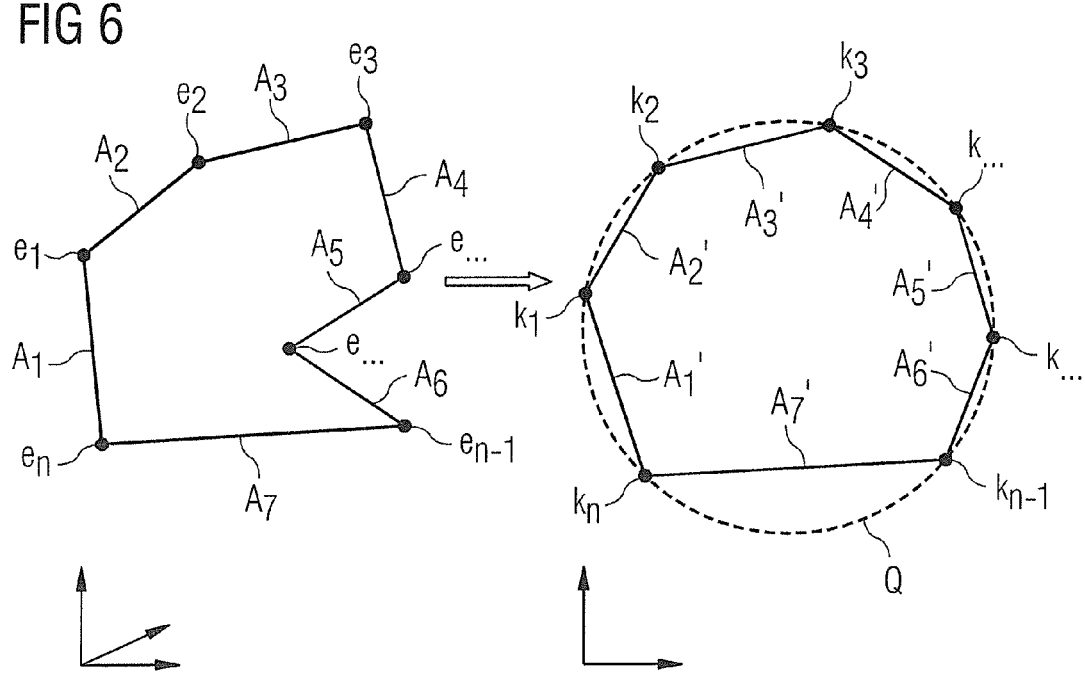
FIG. 6 is a schematic representation of the arrangement of boundary edge points within the scope of a fourth processing step of an exemplary embodiment of the method according to the invention.

The process of the unfolding of the vascular tree 13 is schematically shown in FIG. 6. This planar embedding of the surface model 3 here takes place with the use of an optimization method from the field of mesh parameterization. For efficiency reasons, a method was thereby selected that transfers the edge of the entire surface model 3 into a convex region, here into a circle region Q:

The edge of the surface model 3 is defined by a number n of border edges $e_1, e_2, e_3, \ldots, e_{n-1}, e_n$. They serve as orientation points of the outer boundary of the planar representation of the vascular tree 13. A first line $A_1$ runs between an n-th border edge $e_n$ and a first border edge $e_1$; a second line $A_2$ runs between the first border edge $e_1$ and a second border edge $e_2$. The additional lines $A_3$ through $A_7$ are continued up to the n-th border edge $e_n$ in a continuation of this logic.

The border edges $e1, e_2, e_3, \ldots, e_{n-1}, e_n$ are projected in a plane along the circle region so that analogously numbered projection points border edges $k_1, k_2, k_3, \ldots, k_{n-1}, k_n$ result from these. A first line $A_1'$ runs between an n-th projection point $k_n$ and a first projection point $k_1$; a second line $A_2'$ runs between the first projection point $k_1$ and a second projection point $k_2$. The additional lines $A_3'$ through $A_7'$ are continued up to the n-th projection point $k_n$ in a continuation of this logic. It is important that the lines $A_1$ through $A_7$ from the left representation have exactly the same absolute value in terms of their length as the lines $A_1'$ through $A_7'$ in the right representation. In other words: the border edges $e_1, e_2, e_3, \ldots, e_{n-1}$, $e_n$ are projected in the flat plane such that the distances between them are maintained. Using the border edges projected in such a manner, the surface model 3 is unfolded in a flat plane as described in detail above with the assistance of an averaging method and subsequent resolution of the resulting equation system by means of the Gaussian elimination method and LU decomposition.

The effect of a smoothing of the surfaces of another surface model of a vascular tree is shown using FIGS. 7 through 10 for more detailed illustration.

Figure 7:
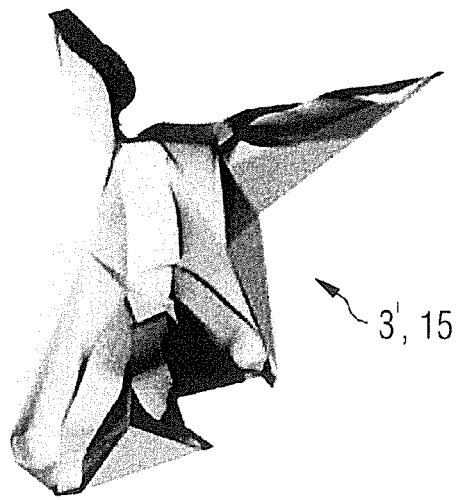
FIG. 7 is a three-dimensional surface model of a different vascular system before a smoothing process.
Figure 8:
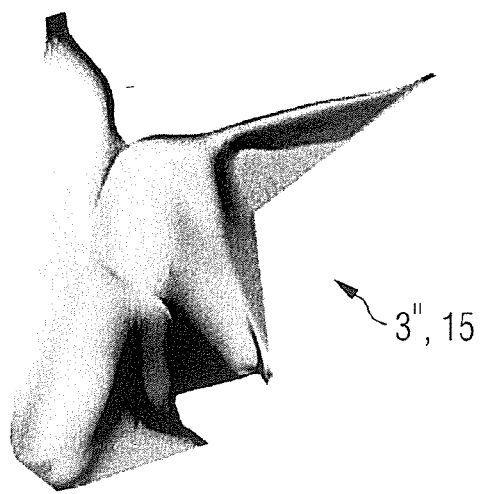
FIG. 8 is a three-dimensional surface model of the vascular system from FIG. 7 after a smoothing process.
Figure 9:
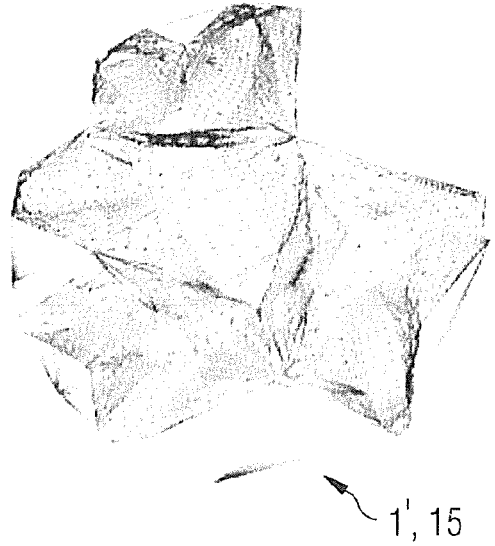
FIG. 9 is a three-dimensional grid model of the vascular system from FIGS. 7 and 8 before the smoothing process.
Figure 10:
FIG. 10 shows the same three-dimensional grid model as in FIG. 9, after the smoothing process.
Figure 11:
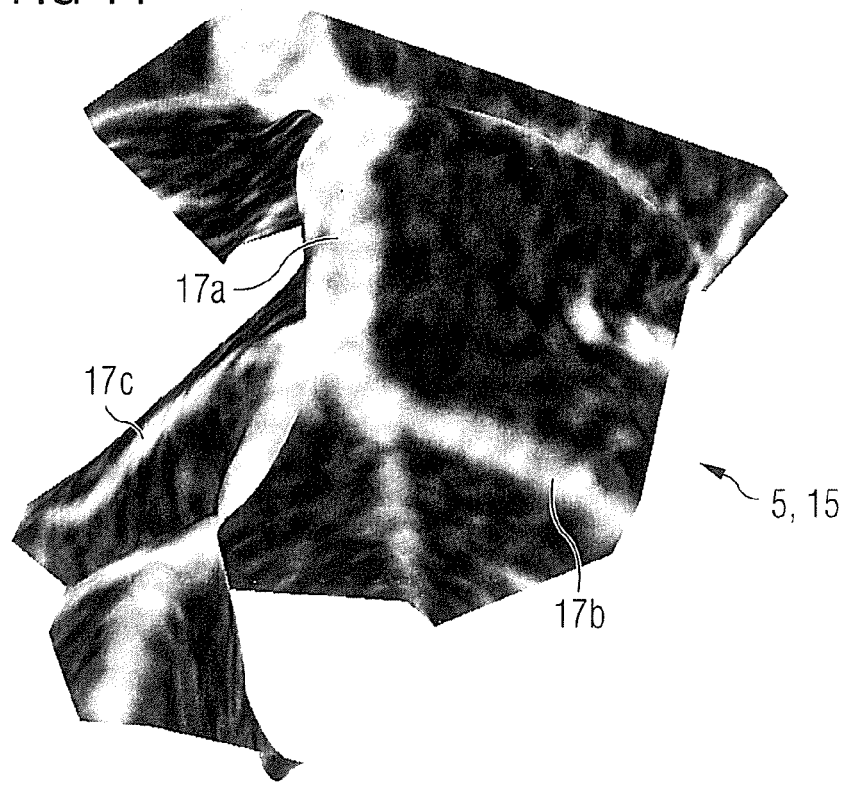
FIG. 11 is a three-dimensional representation of an additional vascular system before the end of the method according to the invention.

FIG. 7 shows in greyscale presentation a section of an unsmoothed surface model 3' of a vascular system 15, and FIG. 8 shows the same surface model 3" smoothed with the aid of a Laplace filter. In FIGS. 9 and 10, this smoothing is shown in unsmoothed form (FIG. 9) and smoothed form (FIG. 10) using a somewhat enlarged section of the corresponding grid models 1' or, respectively, 1". It is apparent that the number of individual surfaces has been significantly reduced, which significantly simplifies the unfolding of the representation as a result.

Figure 12:
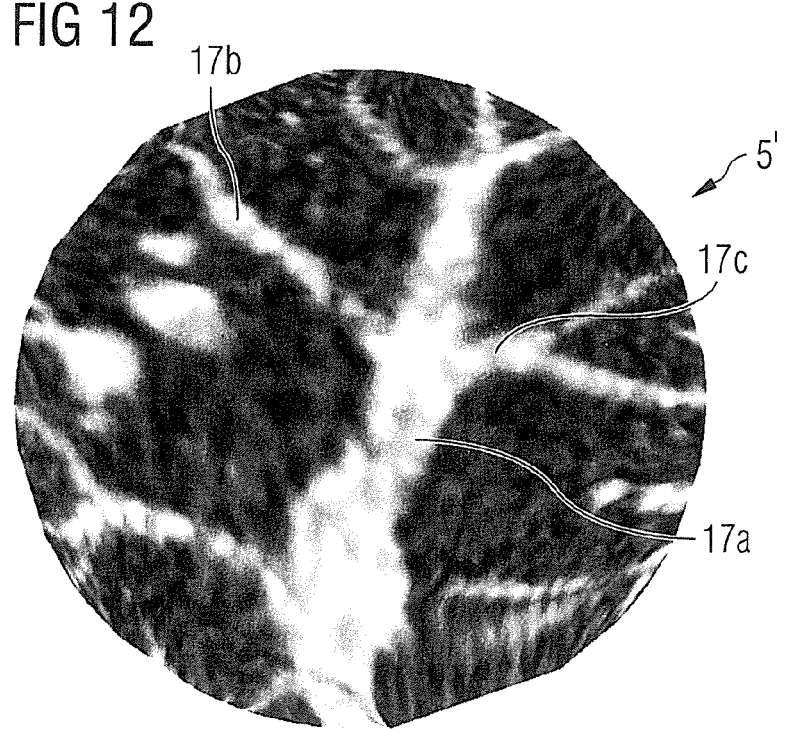
FIG. 12 is a two-dimensional representation of the same vascular system as in FIG. 11, after implementation of one overview image of the method according to the invention.

In the three-dimensional representation 5, FIG. 1 shows a portion of a vascular system 15 in which a few vessels 17a, 17b, 17c are apparent. The corresponding two-dimensional representation 5' rotated by approximately 180° after implementation of an exemplary embodiment of the method according to the invention is shown in FIG. 12. The correspondence of the curves of the vessels 17a, 17b, 17c, and also that the angles of these vessels 17a, 17b, 17c relative to one another have remained essentially unchanged, is clearly apparent. While structures of the vessels 17a, 17b, 17c are thus partially occluded in the three-dimensional representation 5 due to the three-dimensionality, they are all visible in the two-dimensional representation.

Figure 13:
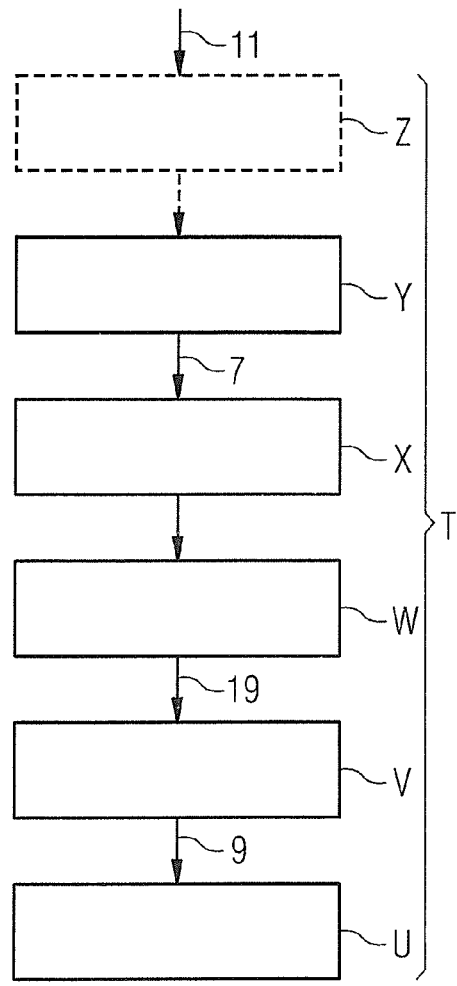
FIG. 13 is a schematic flowchart of the steps of an embodiment of the method according to the invention.

FIG. 13 schematically shows the workflow of an embodiment of a method T according to the invention in a block diagram.

In a first, optional step Z, tomography data 11 are accepted directly from an imaging system or a memory without being prepared for the method T, and then are prepared in the sense of the invention. The prepared tomography data 7 that result from this include the tomography data 11 of a vascular tree 13 in which the vascular tree 13 is segmented at least per region of surrounding structures, and in which are present a number of curve lines 15a, 15b, 15c, 15d, 15e, 15f, 15g, 15h, 15i, 15j, 15k, 15l of vessels 17a, 17b, 17c of the vascular tree 13 that branch with one another. These prepared tomography data 7 are then registered in a second step Y, and in a third step X inlets $B_1, B_2, B_3, B_4, B_5, B_6, B_7, B_8$ are shaped between curve lines 15a, 15b, 15c, 15d, 15e, 15f, 15g, 15h, 15i, 15j, 15k, 15l that are adjacent and/or connected with one another via node points B, C, E, H, M. In a fourth step W, the representation data 19 of the vascular tree 13 are adapted such that the inlets $B_1, B_2, B_3, B_4, B_5, B_6, B_7, B_8$ are arranged flat, adjoining one another in a two-dimensional presentation plane. In a fifth step V, visualization command data 9 are derived from the representation data 19, which visualization command data 9 are output via a visualization unit (a monitor, for example) in a sixth step U for additional processing.

Figure 14:
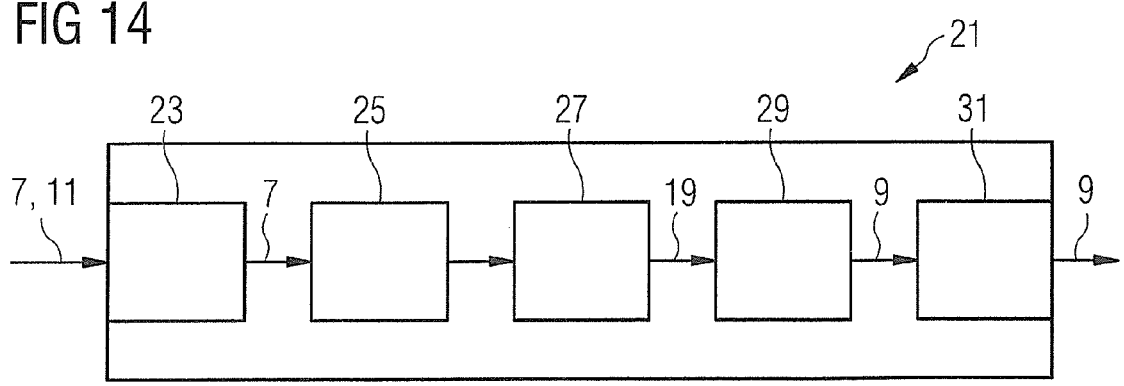
FIG. 14 is a schematic block diagram of an embodiment of the system according to the invention.

In a block presentation, FIG. 14 schematically shows an exemplary embodiment of a system 21 according to the invention for generation of visualization command data 9 that is designed as part of an imaging system, thus a tomography system (not shown). The system 21 comprises a preparation unit 23 to provide prepared tomography data 7. For this, the provision unit 23 can be realized purely as an input interface 23 that already receives pre-prepared tomography data 7, or it can be realized as a preparation unit. In the latter case, it accepts tomography data 11 as described in the optional first step Z and converts them into prepared tomography data 7 in the sense described above.

In a shaping unit 25, inlets are shaped in the prepared tomography data 7 analogous to the third step outlined above. The adaptation unit 27 connected with this implements the fourth step W so that step V can then take place in a derivation unit 29 and an output unit 31 outputs the visualization command data 9.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to generate visualization command data for two-dimensional visualization of a vascular tree of a vascular system from tomography data acquired with an imaging system comprising:

providing a processor with tomography data of a vascular tree, acquired using an imaging system, as prepared tomography data comprising the acquired tomography data of the vascular tree in which the vascular tree is segmented, and in which a plurality of curve lines of the vascular tree are present that branch with respect to one another;

in said processor automatically shaping inlets between curve lines, among said plurality of curve lines, that have a geometrical relationship with respect to each other selected from the group consisting of being adjacent and being connected to each other via respective node points;

in said processor, generating representation data for said vascular tree in which said inlets are arranged so as to be flat and adjoining one another in a two-dimensional presentation plane; and in said processor deriving, directly from said representation data in which said inlets are arranged so as to be flat and adjoining one another in a two-dimensional presentation plane, visualization command data that control a visualized display of said vascular tree, and making said visualization command data available as a data file at an output of said processor in a form for controlling display of said visualized display of said vascular tree.

2. A method as claimed in claim 1 comprising subdividing said inlets into a plurality of individual surfaces.

3. A method as claimed in claim 2 comprising forming at least one of said inlets and said individual surfaces as Coons surfaces.

4. A method as claimed in claim 2 comprising subdividing said inlets into individual surfaces that are respectively bounded by boundary lines that comprise:

a curve line proceeding along a respective individual surface from a first node point to an end point that is a second node point or a curve end point of a curve of said curve line;

a connecting line proceeding from a first node point to a focal point of a respective inlet; and a connecting line proceeding from an end point to a focal point of a respective inlet.

5. A method as claimed in claim 2 comprising adapting a shape of at least one of said inlets and said individual surfaces dependent on a locally present vessel contour of a vessel represented by a locally present curve line.

6. A method as claimed in claim 5 comprising orienting at least one of said inlets and said individual surfaces on vessel contour lines to form a vessel band skeleton by:

(a) inserting individual surfaces between respective curve lines that have said relationship;

(b) making a localized determination of vessel contour lines at a first slice surface of a vessel along a selected curve line;

(c) forming a vertical line along said first slice surface that is at a middle angle between a flat, first individual surface along a second curve line at said flat, first individual surface, and a flat, second individual surface that borders said flat, first individual surface along the selected curve line;

(d) forming a straight auxiliary line that is orthogonal to said vertical line and determining intersection points of said auxiliary line with said vessel contour line on both sides of said vessel contour;

(e) implementing (b) through (d) along a curve of an entire curve line to form two orientation lines from shortest connections of said intersection points along both sides of said vessel contour; and (f) orient the curve of at least one of the individual surfaces and the inlets along the respective orientation lines that are closest to the flat individual surfaces or the inlets.

7. A method as claimed in claim 6 comprising forming each of said surfaces as a Coons surface between two orientation lines associated with a curve line.

8. A method as claimed in claim 1 comprising generating said representation data by:

determining a number of border edges relative to each other;

arranging said borders edges at a same distance relative to each other along a convex outer line; and arranging the inlets as a flat arrangement within said convex outer line, bordered by said convex outer line.

9. A method as claimed in claim 8 comprising generating said flat arrangement using a mean value.

10. A method as claimed in claim 8 comprising generating said flat arrangement by implementing a Gaussian elimination procedure using an LU decomposition.

11. A method as claimed in claim 1 comprising generating said prepared tomography data with said vascular tree segmented at least in regions of branches of said vascular tree and respective surrounding structures.

12. A method as claimed in claim 11 comprising generating said prepared tomography data with said plurality of curve lines of vessels of the vascular tree derived from said segmented regions.

13. A system to generate visualization command data for two-dimensional visualization of a vascular tree of a vascular system from tomography data acquired with an imaging system comprising:

a processor having an input that receives tomography data of a vascular tree, acquired using an imaging system, as prepared tomography data comprising the acquired tomography data of the vascular tree in which the vascular tree is segmented, and in which a plurality of curve lines of the vascular tree are present that branch with respect to one another;

said processor being configured to automatically shape inlets between curve lines, among said plurality of curve lines, that have a geometrical relationship with respect to each other selected from the group consisting of being adjacent and being connected to each other via respective node points;

said processor being configured to generate representation data for said vascular tree in which said inlets are arranged so as to be flat and adjoining one another in a two-dimensional presentation plane;

said processor being configured to derive, directly from said representation data in which said inlets are arranged so as to be flat and adjoining one another in a two-dimensional presentation plane, visualization command data that control a visualized display of said vascular tree; and a display in communication with said processor that receives said visualization command data from an output of said processor and that uses said visualization command data to said visualized display of said vascular tree.

14. A tomography apparatus to generate visualization command data for two-dimensional visualization of a vascular tree of a vascular system from tomography data acquired with an imaging system comprising:

a tomographic image acquisition unit that acquires tomography data of a vascular tree;

a processor provided with said tomography data of said vascular tree, as prepared tomography data comprising the acquired tomography data of the vascular tree in which the vascular tree is segmented, and in which a plurality of curve lines of the vascular tree are present that branch with respect to one another;

said processor being configured to automatically shape inlets between curve lines, among said plurality of curve lines, that have a geometrical relationship with respect to each other selected from the group consisting of being adjacent and being connected to each other via respective node points;

said processor being configured to generate representation data for said vascular tree in which said inlets are arranged so as to be flat and adjoining one another in a two-dimensional presentation plane;

said processor being configured to derive, directly from said representation data in which said inlets are arranged so as to be flat and adjoining one another in a two-dimensional presentation plane, visualization command data that control a visualized display of said vascular tree; and a display in communication with said processor that receives said visualization command data from an output of said processor and that uses said visualization command data to said visualized display of said vascular tree.

15. A non-transitory, computer-readable data storage medium encoded with programming instructions, said storage medium being loaded into a computerized processor and said programming instructions causing said processor to generate visualization command data for a two-dimensional visualization of a vascular tree of a vascular system from tomography data acquired from an imaging system, by:

receiving said tomography data of said vascular tree, acquired using an imaging system, as prepared tomography data comprising the acquired tomography data of the vascular tree in which the vascular tree is segmented, and in which a plurality of curve lines of the vascular tree are present that branch with respect to one another;

shape inlets between curve lines, among said plurality of curve lines that have a geometrical relationship with respect to each other selected from the group consisting of being adjacent and being connected to each other via respective node points;

generate representation data for said vascular tree in which said inlets are arranged so as to be flat and adjoining one another in a two-dimensional presentation plane; and derive, directly from said representation data in which said inlets are arranged so as to be flat and adjoining one another in a two-dimensional presentation plane, visualization command data that control a visualized display of said vascular tree, and make said visualization command data available as a data file at an output of said processor in a form for controlling display of said visualization display.

* * * * *